(12) United States Patent
Black et al.

(10) Patent No.: US 10,794,846 B2
(45) Date of Patent: Oct. 6, 2020

(54) COMBINED WATER CUT AND SALINITY METER

(71) Applicant: Saudi Arabian Oil Company, Dhahran (SA)

(72) Inventors: Michael John Black, Nordrhein-Westfalen (DE); Mohamed N. Noui-Mehidi, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 92 days.

(21) Appl. No.: 16/104,632

(22) Filed: Aug. 17, 2018

(65) Prior Publication Data
US 2019/0003996 A1 Jan. 3, 2019

Related U.S. Application Data

(62) Division of application No. 13/661,941, filed on Oct. 26, 2012, now Pat. No. 10,088,442.
(Continued)

(51) Int. Cl.
*G01N 27/02* (2006.01)
*G06F 15/00* (2006.01)
(Continued)

(52) U.S. Cl.
CPC ........... *G01N 27/02* (2013.01); *G01N 27/221* (2013.01); *G01N 33/18* (2013.01);
(Continued)

(58) Field of Classification Search
CPC ...... G01N 27/02; G01N 33/18; G01N 27/221; G01N 33/2847; G01N 33/2823; G06F 15/00
See application file for complete search history.

(56) References Cited

U.S. PATENT DOCUMENTS 4,226,118 A * 10/1980 Aldrich ................. G01F 23/284
                                                          331/65
4,554,828 A * 11/1985 Doll ....................... G01F 15/18
                                                          73/202
(Continued)

FOREIGN PATENT DOCUMENTS

CA          1247229 A1     12/1988
CN        101294831 A      10/2008
(Continued)

OTHER PUBLICATIONS

A.P. Stogryn, et al., "The Microwave Dielectric Properties of Sea and Fresh Water," GenCorp Aerojet, Azusa, CA (1995) (24 pages).
(Continued)

*Primary Examiner* — Stephanie E Bloss
(74) *Attorney, Agent, or Firm* — Bracewell LLP; Constance Gall Rhebergen (57) ABSTRACT

Disclosed is a flow meter and method for measuring water cut and salinity of a multiphase mixture. The water-cut meter includes a conduit configured to receive the multiphase mixture, and a probe array configured to measure a cross-sectional area of the conduit. The probe array includes a plurality of coaxial probes connected in parallel. Optionally, the probe array is configured to operate at a single high frequency, for example, 1 to 3 GHz, to minimize conductivity loss relative to capacitance. The flow meter further includes a processor configured to transmit a signal to the probe array and to receive a reflected signal from the probe array using a single channel. The processor is further configured to calculate the water cut and the salinity of the multiphase mixture based on a single complex permittivity of the multiphase mixture calculated from the received reflected signal.

6 Claims, 4 Drawing Sheets

Related U.S. Application Data (60) Provisional application No. 61/552,646, filed on Oct. 28, 2011.

(51) Int. Cl.
*G01N 33/28* (2006.01)
*G01N 27/22* (2006.01)
*G01N 33/18* (2006.01)

(52) U.S. Cl.
CPC ..... *G01N 33/2823* (2013.01); *G01N 33/2847* (2013.01); *G06F 15/00* (2013.01)

(56) References Cited

U.S. PATENT DOCUMENTS

| | | | | |
|---|---|---|---|---|
| 5,675,259 | A * | 10/1997 | Arndt | G01F 1/66 324/642 |
| 6,831,470 | B2 * | 12/2004 | Xie | G01N 27/06 324/693 |
| 6,883,389 | B2 | 4/2005 | Eldridge | |
| 6,915,707 | B2 * | 7/2005 | Nyfors | G01F 1/40 73/861.63 |
| 6,945,095 | B2 | 9/2005 | Johansen | |
| 7,143,638 | B1 | 12/2006 | Scott | |
| 7,334,450 | B1 | 2/2008 | Scott | |
| 8,916,815 | B2 * | 12/2014 | Xie | G01N 21/33 250/256 |
| 2007/0279073 | A1 * | 12/2007 | Wee | G01N 33/2823 324/639 |
| 2009/0204346 | A1 * | 8/2009 | Xie | G01F 1/66 702/45 |

FOREIGN PATENT DOCUMENTS

| | | |
|---|---|---|
| WO | 2008029025 A1 | 3/2008 |
| WO | 2010106354 A1 | 9/2010 |

OTHER PUBLICATIONS

International Search Report and Written Opinion for related PCT Application PCT/US2012/062129, dated Aug. 13, 2013.
Hilland, J., et al., Simple Sensor System for Measuring the Dielectric Properties of Saline Solutions, Measurement Science and Technology, Aug. 1, 1997, pp. 901-910, vol. 8., IOP Publishing, LTD.
R. Somaraju and J. Trumpf "Frequency, Temperature, and Salinity Variation of the Permittivity of Seawater" IEEE Trans. On Ant. And Prop. 54(11) 2006 (8 pages).
Strazza, et al., "Capacitance Sensor for Hold-Up Measurement in High-Viscous-Oil/Conductive-Water Core-Annular Flows," Flow Measurement and Instrumentation, 22 (5): pp. 360-369, Oct. 2011.
T. Meissner and F. J. Wentz, "The Complex Dielectric Constant of Pure and Sea Water from Microwave Satellite Observations," IEEE Trans. On Geosc. And Rem. Sens 42(9) 2004, pp. 1836-1849.

* cited by examiner

COMBINED WATER CUT AND SALINITY METER

RELATED APPLICATION

This application is a divisional application of U.S. patent application Ser. No. 13/661,941, filed on Oct. 26, 2012, which claims priority to U.S. Provisional Patent Application No. 61/552,646, filed on Oct. 28, 2011, the disclosure of which is incorporated herein by reference in its entirety.

BACKGROUND

Field of the Invention

Embodiments of the invention relate to a flow meter or a water cut meter (hereinafter collectively referred to as a "flow meter") for measuring water cut and salinity levels of a multiphase mixture, and more particularly to a flow meter including a coaxial probe array which determines in real-time the presence of multiphase flow in a mixture and water cut and salinity levels of a multiphase mixture having a high salinity concentration.

Description of the Related Art

Real-time water cut and salinity measurements of multiphase mixtures are highly demanded by daily operations for both reservoir management and production allocation in the oil and gas industry. Conventional flow meters are limited by water cut measurement ranges and the level of salinity found in multiphase mixtures. For example, reservoir and completion brines are commonly observed to have salinity levels greater than the salinity of sea water, which typically has a salinity level of about 35 parts per thousand (ppt). In some cases, the salinity level of reservoir and completion brines range from about 100 ppt to about 200 ppt, and has been observed at a saturation concentration of 360 ppt. Connate water has also been commonly observed to have salinity levels greater than the salinity of sea water. In some cases, the salinity level of connate water has been observed at around 200 ppt.

The measurement of permittivity (i.e., relative dielectric constant) is a means for estimating the aqueous phase(s) of a multiphase mixture. In particular, permittivity measurement using capacitance or microwave sensors is a common process for estimating water cut and salinity of the multiphase mixture. Capacitance is observed to increase between a pair of electrodes as the amount of water between the electrodes increases. The effect of increasing the salinity of the water in a multiphase mixture is to introduce a parallel conduction path between the electrodes which inhibits a measurement of capacitance at low frequencies where the imaginary component of permittivity exceeds a value of 300. Thus, capacitance-based water cut measurements are observed to fail at high levels of salinity. As a result, salinity variation causes the inaccuracy of water cut measurements, preventing well production optimization within the capacity constraints of production facilities.

Electromagnetics sensors have been designed to more accurately measure the water cut or water-in-liquid ratio (WLR) of multiphase mixtures (e.g., oil-water or oil-water-gas multiphase fluids, as non-limiting examples). In some industrial and scientific applications, electromagnetic coaxial probes have been used to measure water cut in both single phase and multiphase mixtures encountered in oilfields, based on the principle that the measured complex reflection coefficient (i.e., ratio of reflected signal to the incident signal) is dependent on the aperture impedance (i.e., complex permittivity) of a sample material terminating the probe.

One such sensor includes a single microwave, open-ended coaxial reflection probe which measures the permittivity and conductivity of a multiphase mixture and combines the measured mixture permittivity and conductivity with a known or derived relationship between brine water conductivity and brine water permittivity to estimate the on-line brine water conductivity of the mixture. The probe is mounted at an opening of a production pipe wall, and thus only measures a small subset of the overall cross-section of the production pipe (i.e., a small measurement area of the permittivity and conductivity of the multiphase mixture).

Another such sensor includes one or more open-coaxial probes, operating at about 1 GHz, arranged along the diameter of, or affixed to a column in, a production pipe. Each probe detects an amplitude and a phase of a reflected signal for identifying single phase and multiphase mixtures based on the differences between the real part of each mixture's complex permittivity. Each probe requires a set of electronics to measure the complex permittivity of the respective mixture.

In order to effectively optimize well production within the constraints of production facilities, flow meters providing more accurate water cut and salinity measurements for multiphase mixtures having high salinity concentrations will need to be developed for the oil and gas industry.

SUMMARY

Embodiments of the invention are directed to a flow meter for measuring water cut and salinity of a multiphase mixture and for detecting multiphase flow in a mixture for well production in the oil and gas industry. In particular, provided herein is a flow meter for measuring the water cut and salinity of a multiphase mixture having a high salinity level. In certain embodiments, the flow meter includes a high frequency, coaxial probe array having a plurality of probes combined in parallel that is collectively driven by a single set of driver electronics. In accordance with certain embodiments of the invention, the flow meter determines, in real-time, the presence of multiphase flow in a mixture and measures water cut and salinity levels of the multiphase mixture across a cross-sectional area of a production conduit.

In accordance with an embodiment of the invention, there is provided a flow meter for measuring water cut and salinity of a multiphase mixture. The flow meter includes a conduit configured to receive the multiphase mixture, and a probe array configured to measure a cross-sectional area of the conduit. The probe array includes a plurality of coaxial probes connected in parallel. The flow meter further includes a processor configured to ground all but one of the coaxial probes in the probe array, transmit a signal to the probe array, and receive a reflected signal from the probe array. The processor is further configured to transmit the signal and receive the reflected signal using a single channel between the probe array and the processor. Further, the processor is configured to calculate the water cut and the salinity of the multiphase mixture based on a single complex permittivity of the multiphase mixture calculated from the received reflected signal of each non-grounded coaxial probe. The single complex permittivity is an average of the complex permittivity of the multiphase mixture measured by each non-grounded coaxial probe. In some embodiments, the processor is further configured to perform an interpolation between the complex permittivity of the multiphase mixture measured by each non-grounded coaxial probe to generate a single continuous function of complex permittivity throughout the cross-sectional area of the conduit. In some embodiments, the interpolation is a linear or bilinear interpolation. In some embodiments, the plurality of coaxial probes are arranged in a two-dimensional plane.

In accordance with another embodiment of the invention, there is provided a method for measuring water cut and salinity of a multiphase mixture. The method includes the steps of receiving, using a conduit, the multiphase mixture, and measuring, using a probe array, a cross-sectional area of the conduit. The probe array includes a plurality of coaxial probes connected in parallel. The method further includes the steps of grounding all but one of the coaxial probes in the probe array, transmitting a signal to the probe array, and receiving a reflected signal from the probe array. In accordance with this embodiment of the invention, the signal is transmitted and the reflected signal is received using a single channel between the probe array and the processor. Further, the method includes the step of calculating, using a processor, the water cut and the salinity of the multiphase mixture based on a single complex permittivity of the multiphase mixture calculated from the received reflected signal of each non-grounded coaxial probe. In accordance with this embodiment of the invention, the single complex permittivity is an average of the complex permittivity of the multiphase mixture measured by each non-grounded coaxial probe. In some embodiments, the method further includes the step of performing an interpolation between the complex permittivity of the multiphase mixture measured by each non-grounded coaxial probe to generate a continuous function of complex permittivity throughout the cross-sectional area of the conduit.

BRIEF DESCRIPTION OF DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

Although the following detailed description contains many specific details for purposes of illustration, it is understood that one of ordinary skill in the relevant art will appreciate that many examples, variations, and alterations to the following details are within the scope and spirit of the invention. Accordingly, the exemplary embodiments of the invention described herein are set forth without any loss of generality, and without imposing limitations, relating to the claimed invention. Like numbers refer to like elements throughout. Prime notation, if used, indicates similar elements in alternative embodiments.

Embodiments of the invention are directed to a flow meter (i.e., a water cut meter) including a coaxial probe array that can be utilized with a variety of AC measurement methods in a high frequency range to determine water cut and salinity of a multiphase mixture based on an impedance measurement, for example, a single complex permittivity of the multiphase mixture. The device functions at levels of salinity which would preclude the functioning of conventional capacitance water cut meters. The coaxial probe array, in accordance with certain embodiments of the invention, may be integrated as an in-line device, where a plurality of probes can be connected in parallel around the circumference of a conduit, for example, a 3.5" production tube, for measuring properties of a multiphase mixture across a cross-sectional area of the conduit. In accordance with an embodiment of the invention, the plurality of probes in the coaxial probe array are collectively driven by a single set of electronics (i.e., electromagnetic transmission of signals to and from the coaxial probe array occur over a single electronics channel). Embodiments of the invention are also directed to a flow meter including a coaxial probe array that determines the presence of multiphase flow in a mixture based on the average complex permittivity of the mixture.

As used herein, the term "multiphase" shall be used to describe a mixture including multiple components, such as oil-water, oil-water-gas, water-solids, as non-limiting examples. The term "conductivity" shall be interchangeable with equivalent terms, such as "resistivity", as a non-limiting example. The term "permittivity" shall refer to a value relative to a vacuum, which may be commonly referred to as a dielectric constant. The term "complex permittivity" (also commonly referred to as "complex relative permittivity") shall refer to a complex value with its real part or component being related to permittivity and its imaginary part or component being related to permittivity loss (i.e., conductivity loss through the multiphase mixture). The term "conduit" or "production conduit" shall be used to describe a wellbore through which production fluids are produced (i.e., travel).

Figure 1:
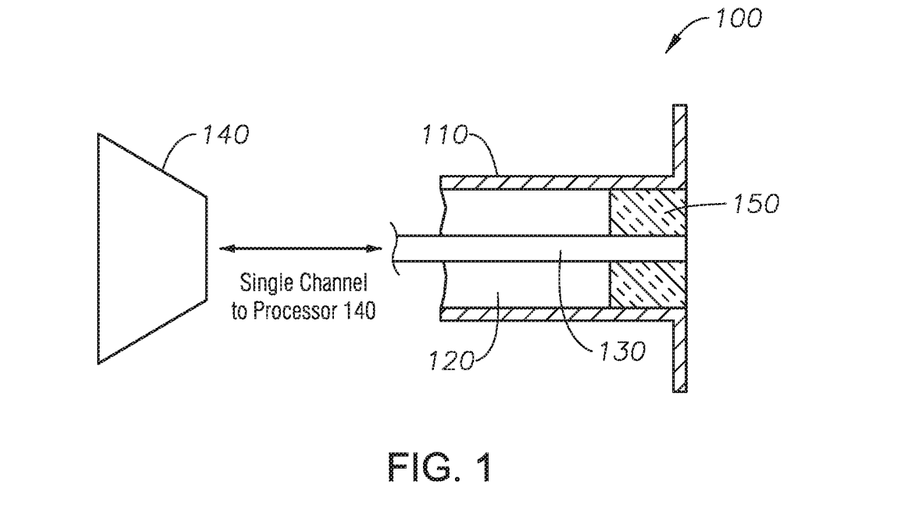
FIG. 1 is a schematic diagram of a flow meter including a probe array for measuring an impedance characteristic of a multiphase mixture flowing through a conduit, in accordance with an embodiment of the invention.

FIG. 1 is a schematic diagram of a flow meter including a probe array for measuring an impedance characteristic of a multiphase mixture flowing through a conduit, in accordance with an embodiment of the invention. As shown in FIG. 1, flow meter 100 is provided for measuring water cut and salinity of a multiphase mixture. In accordance with an embodiment of the invention, the flow meter 100 includes conduit 110 to receive the multiphase mixture, and probe array 120 to measure a cross-sectional area of the conduit 110. One of ordinary skill in the relevant art would understand that the conduit discussed below for the various embodiments of the invention can be constructed in any shape and/or size commonly used in the oil and gas industry (e.g., a 3.5" diameter production conduit used in a wellbore for petroleum production).

According to certain embodiments of the invention, the probe array 120 includes a plurality of coaxial probes 130 connected in parallel, as will be discussed in more detail below. It should be noted that, while FIG. 1 illustrates only one coaxial probe 130 of the probe array 120, various embodiments of the invention may include different geometries (i.e., two or more coaxial probes 130) for the probe array 120, as will be discussed in more detail below and illustrated at least in FIGS. 3 and 4.

Each coaxial probe 130 can have an open-ended or closed design and can measure the dielectric properties of the multiphase mixture over a range of radio and microwave frequencies, for example, 1 to 3 MHz, as a non-limiting example. The flow meter 100 further includes processor 140 to transmit an electromagnetic signal to the probe array 120 and to receive a reflected electromagnetic signal from the probe array 120 for measuring an impedance characteristic (e.g., complex permittivity, as a non-limiting example) of the multiphase mixture. In accordance with certain embodiments of the invention, the processor 140 calculates the water cut and the salinity of the multiphase mixture based on the complex permittivity of the multiphase mixture calculated from the received reflected signal, as will be discussed in more detail below.

Conventional water cut meters incorporating a single probe are only able to measure a small subset of a cross-sectional area of a production conduit, and therefore are unable to accurately measure the water cut and salinity of the multiphase mixture, especially mixtures having a high salinity concentration. In order to overcome this deficiency of conventional water cut meters, the flow meter 100, according to various embodiments of the invention, includes the plurality of coaxial probes 130 being connected in parallel. The parallel configuration for the plurality of coaxial probes 130 enables the flow meter 100 to determine the complex permittivity for the multiphase mixture across the entire cross-sectional area of the conduit 110 as a single parameter, thereby minimizing the need for a parallel driver and processing electronics for each coaxial probe 130. By eliminating additional drivers and processing electronics, the probe array 120 and the plurality of coaxial probes 130 of the flow meter 100 can be incorporated as an in-line device in the conduit 110.

In order to measure the water cut and salinity of a multiphase mixture having a high salinity concentration, the processor 140, according to an embodiment of the invention, operates at a single high frequency range, for example, 1 to 3 gigahertz (GHz), as a non-limiting example, so that the salinity signal (i.e., conductivity loss) does not inhibit the water cut signal (i.e., capacitance). Using the signal transmitted to the probe array 120 and the reflected signal received from the probe array 120, the processor 140 determines the water cut and salinity of the multiphase mixture across a cross-sectional area of the conduit 110 by measuring a total reflected power from the probe array 120, thus providing a complex permittivity or impedance of the mixture that adds up to a larger value than that measured by a conventional water cut meter. This complex permittivity represents a function of the average complex permittivity of the multiphase fluid present in front of each coaxial probe 130 across the entire cross-sectional area of the conduit 110.

In accordance with an embodiment of the invention, the real part or component of the complex permittivity (which is related to capacitance) varies as a function of a water-oil ratio, while the imaginary part or component of the complex permittivity (which is related to conductivity) varies as a function of the amount of mobile salt ions within the water. According to various embodiments, the processor 140 calculates the capacitance and the conductivity of the multiphase mixture based on the real component and the imaginary component, respectively, of the single complex permittivity of the multiphase mixture. The processor 140 further determines the water cut and salinity of the multiphase mixture based on the calculated capacitance and conductivity values for the multiphase mixture. In accordance with an embodiment of the invention, the capacitance and the conductivity represent an average capacitance and an average conductivity, respectively, of the multiphase mixture measured by the plurality of coaxial probes 130.

In accordance with certain embodiments of the invention, the complex permittivity can be represented by frequency, temperature, and salinity dependent models as described in any of the following non-patent literature: (1) A. P. Stogryn, et al., "The Microwave Dielectric Properties of Sea and Fresh Water," Gen Corp Aerojet, Azusa, C A (1995); (2) T. Meissner and F. J. Wentz, "The Complex Dielectric Constant of Pure and Sea Water from Microwave Satellite Observations," IEEE Trans. On Geosc. And Rem. Sens. 42(9) (2004), pp. 1836-1849; or (3) R. Somaraju and J. Trumpf, "Frequency, Temperature, and Salinity Variation of the Permittivity of Seawater," IEEE Trans. On Ant. And Prop. 54(11) (2006).

For example, for a capacitor model, the capacitance of a parallel plate capacitor of area A and separation d with saline water at temperature T and salinity S may be represented by equation (1):

$$C(f, T, S) = 2\pi\varepsilon_0 K(f, T, S)\frac{A}{d} \qquad (1)$$

The complex impedance of the parallel plate capacitor may be represented by equation (3):

$$X = \frac{1}{i2\pi f(f, T, S)} = a + ib \qquad (2)$$

where a is resistance which is related to the imaginary component of K and b is a capacitance which is related to the real component of K.

Oil's permittivity is close to 1 and has zero conductivity ($\sigma=0$), so in an oil-water mixture the capacitance, b, is a measure of the amount of water present and the conductivity is a measure of the overall conductivity of the mixture, assuming that a is known.

Figure 2:
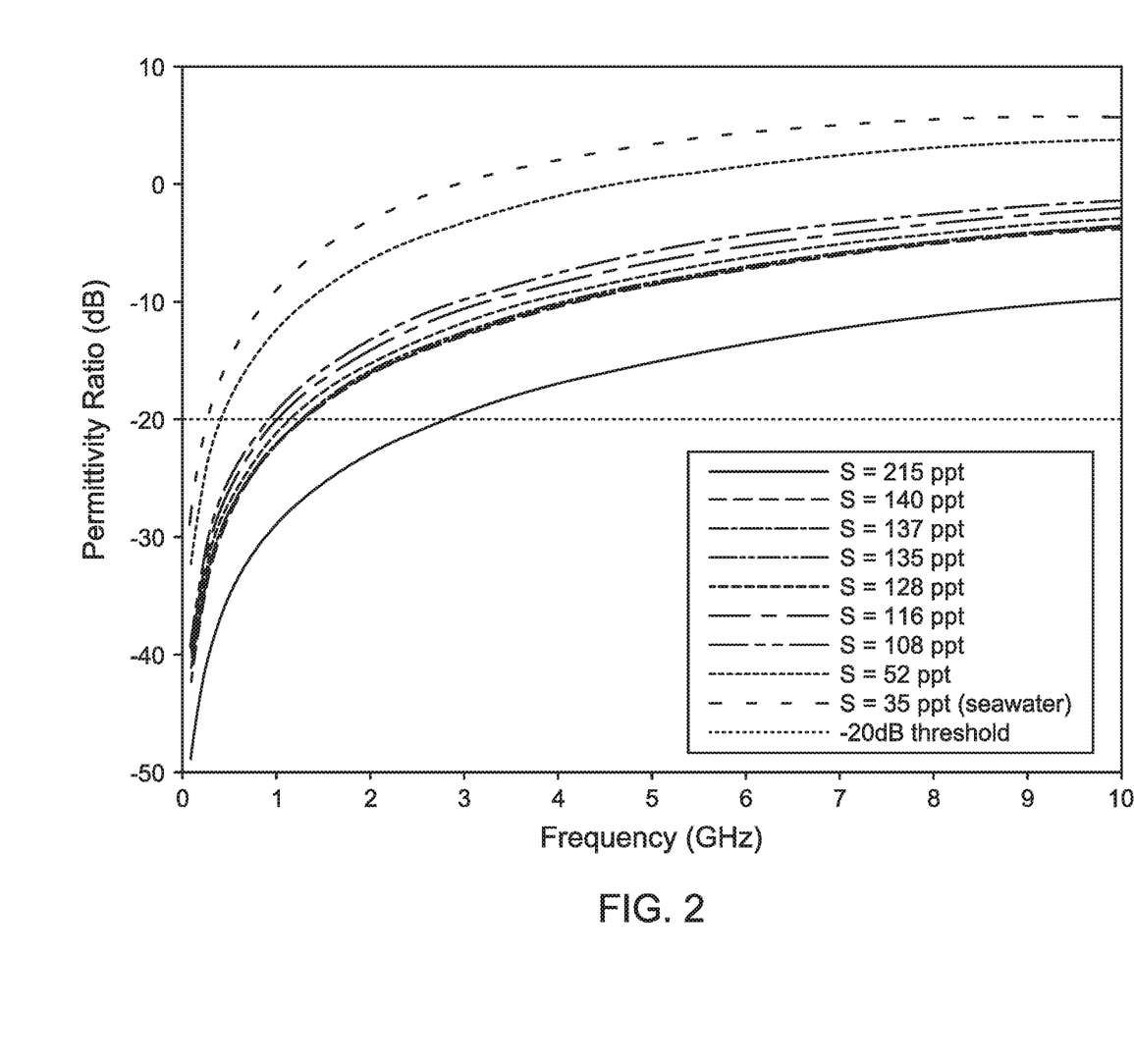
FIG. 2 is a graph showing permittivity ration (b/a) as a function of increasing frequency at a fixed temperature T=60° C. for salinities determined according to certain embodiments of the invention.

FIG. 2 is a graph showing permittivity ration (b/a) as a function of increasing frequency at a fixed temperature T=60° C. for salinities determined according to certain embodiments of the invention. FIG. 2 illustrates that at low frequencies, the capacitance signal is very small relative to the salinity conductivity, resulting in a very small b/a ratio. The small b/a ratio indicates that the measurement system (i.e., convention water cut meters) has insufficient dynamic range at low frequency to determine b, and hence the water cut at high salinity levels. This suggests that better results for determining water cut, as well as salinity levels, of a multiphase mixture with high salinity levels can be obtained by increasing the frequency above 1 GHz. However, at very high frequencies where f>3 GHz, the excitation frequency becomes comparable with the relaxation frequency of the water and sets an upper limit to the measurement frequency of the flow meter according to embodiments of the invention.

In accordance with an embodiment of the invention, the processor 140, as shown in FIG. 1, further adjusts a propagation delay through the probe array 120 to facilitate the transmission and receipt of the electromagnetic signals between the probe array 120 and the processor 140. The processor 140 also measures scattering parameters (e.g., S-parameters) in the received reflected signal.

Optionally, the conduit 110, as further shown in FIG. 1, is made of a metallic material, for example, a corrosion-resistant alloy, such as a carbon steel conduit coated with a corrosion inhibitor, as a non-limiting example.

Optionally, the conduit 110, as further shown in FIG. 1, includes a flow diffuser (not shown) contained therein for controlling the flow of the multiphase mixture through the conduit 110 and across the probe array 120 for sampling the multiphase mixture to determine, for example, the complex permittivity of the multiphase mixture across the entire cross-sectional area of the conduit 110. In accordance to some embodiments, the flow diffuser also homogenizes the multiphase mixture in the conduit 110.

Figure 3:
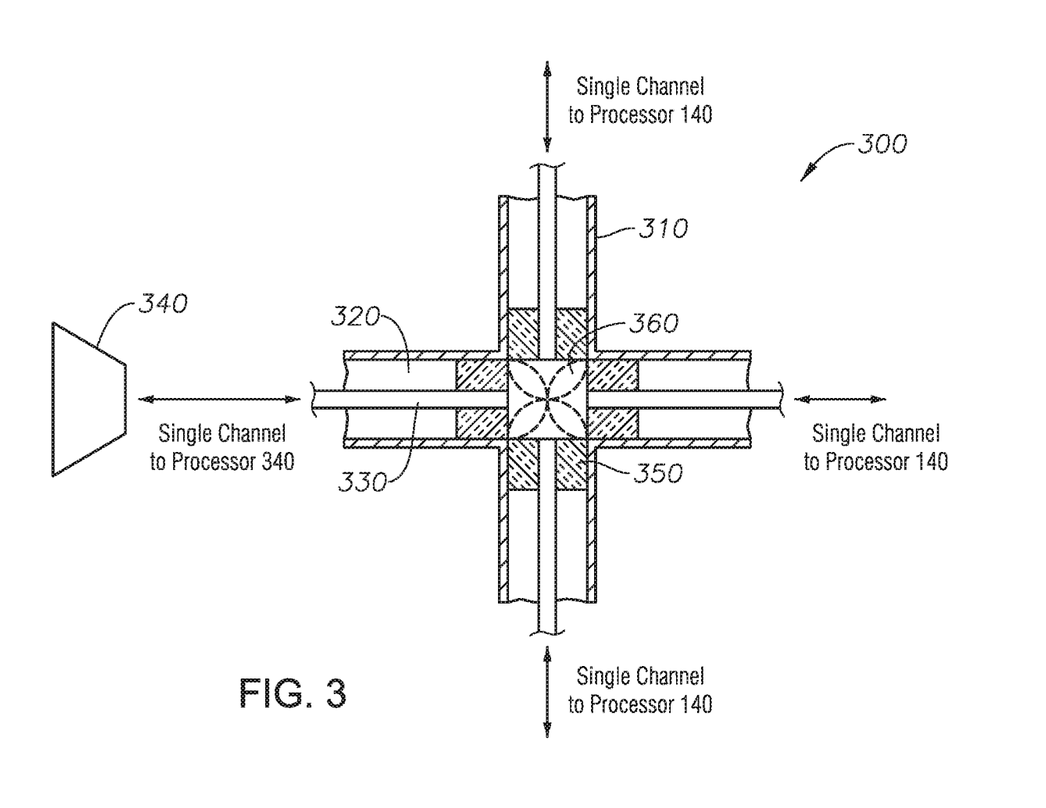
FIG. 3 is a schematic diagram of a quad geometry flow meter including a quad geometry probe array for measuring an impedance characteristic of a multiphase mixture flowing through a square-shaped conduit, in accordance with an embodiment of the invention.

As briefly noted above, various embodiments of the invention may include different geometries for the probe array. FIG. 3 is a schematic diagram of a quad geometry flow meter including a quad geometry probe array for measuring an impedance characteristic of a multiphase mixture flowing through a square-shaped conduit, in accordance with an embodiment of the invention. In accordance with at least one embodiment, the quad geometry flow meter 300, as shown in FIG. 3, includes a quad geometry conduit 310 to receive the multiphase mixture, and a quad geometry probe array 320 to measure a cross-sectional area of the quad geometry conduit 310. In accordance with an embodiment of the invention, the quad geometry probe array 320 includes a plurality of quad geometry coaxial probes 330 connected in parallel. As similarly discussed above for FIG. 1, each quad geometry coaxial probe 330 has an open-ended or closed design and can measure the dielectric properties of the multiphase mixture over a range of radio and microwave frequencies, for example, 1 to 3 MHz, as a non-limiting example.

In accordance with an embodiment of the invention, the quad geometry flow meter 300 further includes a quad geometry processor 340 to transmit an electromagnetic signal to the quad geometry probe array 320 and to receive a reflected electromagnetic signal from the quad geometry probe array 320 for measuring an impedance characteristic (e.g., complex permittivity, as a non-limiting example) of the multiphase mixture. In accordance with certain embodiments of the invention, the quad geometry processor 340 calculates the water cut and the salinity of the multiphase mixture based on the complex permittivity of the multiphase mixture calculated from the received reflected signal, as discussed above for FIG. 1.

Optionally, the conduit 310, as further shown in FIG. 3, includes a flow diffuser 360 contained therein for controlling the flow of the multiphase mixture through the conduit 310 and across the probe array 320 for sampling the multiphase mixture to determine, for example, the complex permittivity of the multiphase mixture across the entire cross-sectional area of the conduit 310. In accordance to some embodiments, the flow diffuser also homogenizes the multiphase mixture in the conduit 310.

Figure 4:
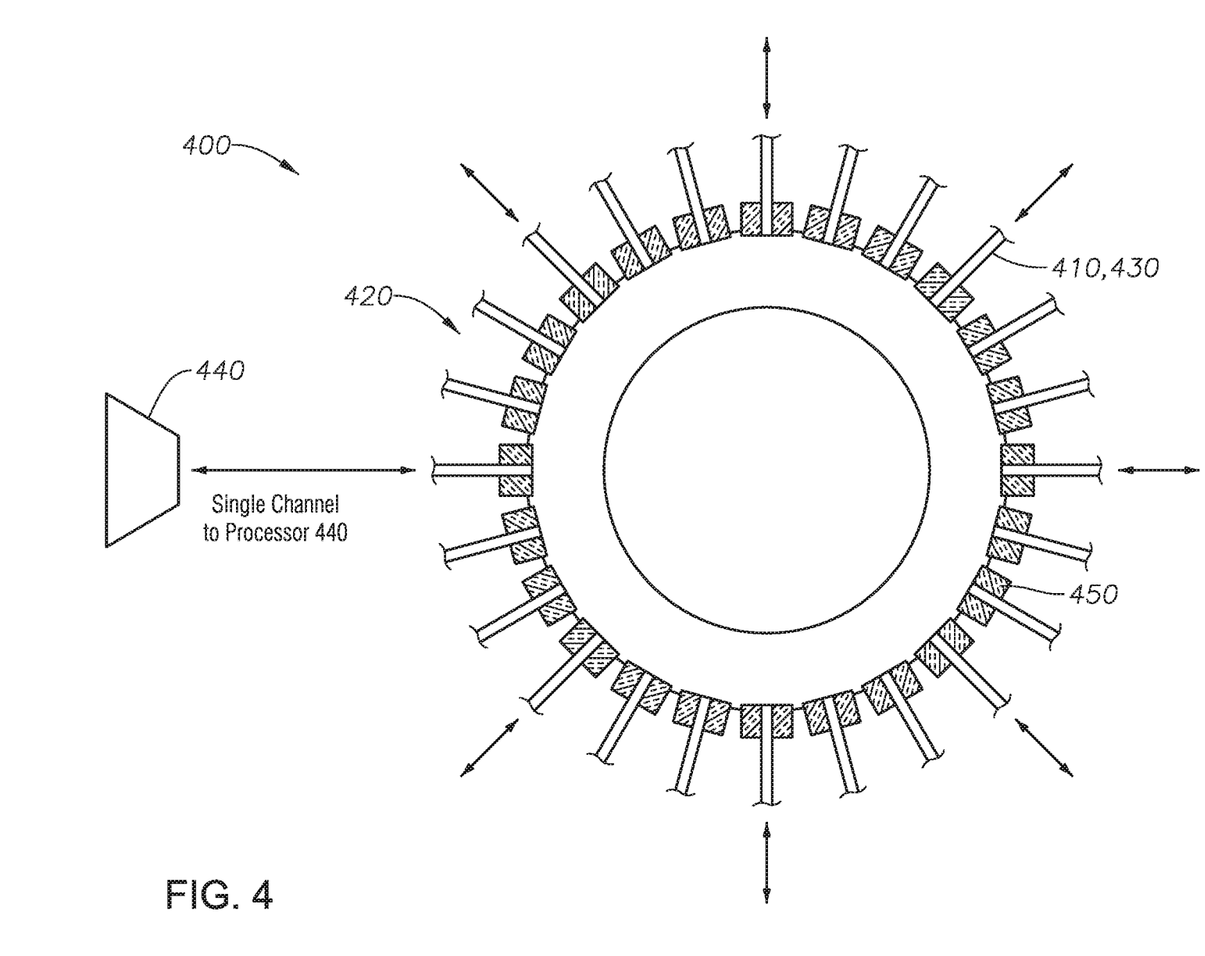
FIG. 4 is a schematic diagram of a probe array flow meter including a multi-coaxial probed probe array for measuring an impedance characteristic of a multiphase mixture flowing through a cylindrical conduit, in accordance with an embodiment of the invention.

FIG. 4 is a schematic diagram of another probe array flow meter including a multi-coaxial probed probe array for measuring an impedance characteristic of a multiphase mixture flowing through a cylindrical conduit, in accordance with an embodiment of the invention. In accordance with an embodiment of the invention, each of the coaxial probes 430 of the probe array flow meter 400 individually measures a complex permittivity of the multiphase mixture, which is an average value based on the relative amounts of water and oil within a measurement area in front of each coaxial probe 430. Combining the coaxial probes 430 together in parallel electrically generates a single measured electromagnetic signal from which the overall average permittivity of the multiphase mixture across the entire cross-sectional area of the conduit 410 can be determined. As shown in FIGS. 3 and 4, each coaxial probe 330, 430 has a small measurement area relative to the cross-sectional area of the conduits 310, 410, respectively. As further shown in FIGS. 3 and 4, each of the probe arrays 320, 420 further includes one or more separators 350, 450 (i.e., an insulator), for spacing each of the coaxial probes 330, 430 from one another across the cross-sectional area of the conduits 310, 410, respectively. According to certain embodiments of the invention, each of the separators 350, 450 spaces the coaxial probes 330, 430 across the cross-sectional area of the conduits 310, 410 based on a length scale of a multiphase phenomenon that the probe arrays 320, 420 are measuring.

Optionally, the conduit 410, as further shown in FIG. 4, includes a flow diffuser (not shown) contained therein for controlling the flow of the multiphase mixture through the conduit 410 and across the probe array 420 for sampling the multiphase mixture to determine, for example, the complex permittivity of the multiphase mixture across the entire cross-sectional area of the conduit 410. In accordance to some embodiments, the flow diffuser also homogenizes the multiphase mixture in the conduit 410.

Figure 5:
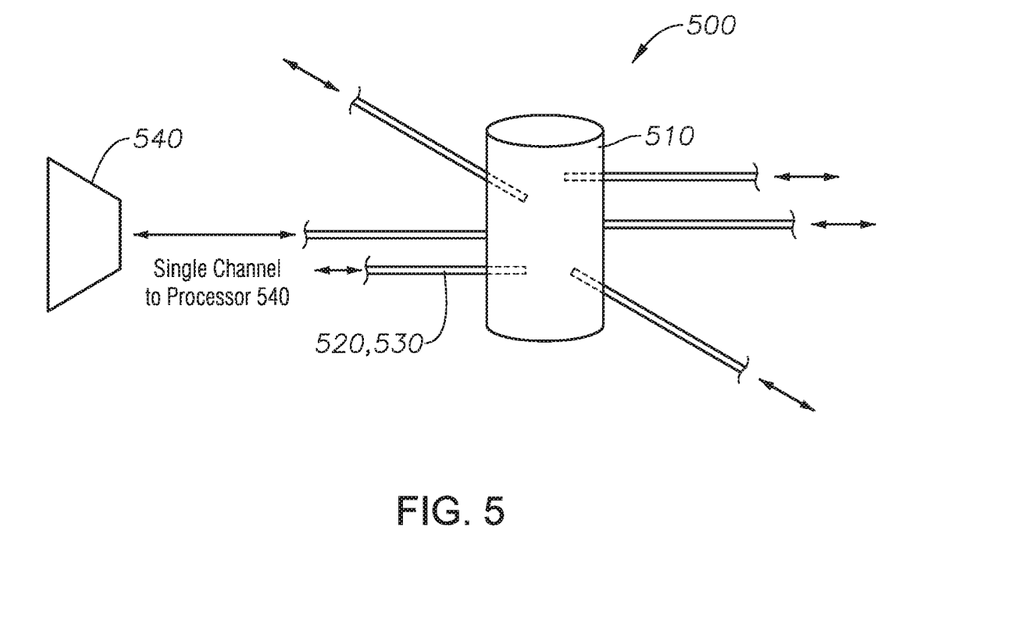
FIG. 5 is a schematic diagram of a probe-grounded flow meter including a probe array for measuring an impedance characteristic of a multiphase mixture flowing through a conduit, in accordance with an embodiment of the invention.

FIG. 5 is a schematic diagram of a probe-grounded flow meter including a probe array for measuring an impedance characteristic of a multiphase mixture flowing through a conduit, in accordance with an embodiment of the invention. As shown in FIG. 5, the probe-grounded flow meter 500 includes a conduit 510 to receive the multiphase mixture, and a probe-grounded probe array 520 that measures a cross-sectional area of the conduit 510. The probe-grounded probe array 520 includes a plurality of coaxial probes 530 connected in parallel. In accordance with certain embodiments of the invention, the probe-grounded flow meter 500 further includes a probe-grounding processor 540 that grounds all but one of the coaxial probes 530 in the probe-grounded probe array 520, transmits an electromagnetic signal to the probe-grounded probe array 520, and receives a reflected electromagnetic signal from the probe-grounded probe array 520. The probe-grounding processor 540 transmits the electromagnetic signal and receives the reflected electromagnetic signal using a single channel between the probe-grounded probe array 520 and the probe-grounding processor 540. Further, the probe-grounding processor 540 calculates the water cut and the salinity of the multiphase mixture based on a single complex permittivity of the multiphase mixture calculated from the received reflected electromagnetic signal of each non-grounded coaxial probe 530. In accordance with certain embodiments of the invention, the single complex permittivity is an average of the complex permittivity of the multiphase mixture measured by each non-grounded coaxial probe 530.

Optionally, the probe-grounding processor 540 further performs an interpolation between the complex permittivity of the multiphase mixture measured by each non-grounded coaxial probe 530 to generate a single continuous function of complex permittivity throughout the cross-sectional area of the conduit 510. According to various embodiments, the interpolation includes, for example, one of a linear or bilinear interpolation. One of ordinary skill in the art would have understood that a determination of whether to use a linear or bilinear interpolation is based on, for example, minimization of computational overhead, as a non-limiting example. As further shown in FIG. 5, the plurality of coaxial probes 530 is arranged in a two-dimensional plane, and is not necessarily aligned at right angles to the central axis of the conduit 510.

Optionally, the conduit 510, as further shown in FIG. 5, includes a flow diffuser (not shown) contained therein for controlling the flow of the multiphase mixture through the conduit 510 and across the probe array 520 for sampling the multiphase mixture to determine, for example, the complex permittivity of the multiphase mixture across the entire cross-sectional area of the conduit 510. In accordance to some embodiments, the flow diffuser also homogenizes the multiphase mixture in the conduit 510.

Figure 6:
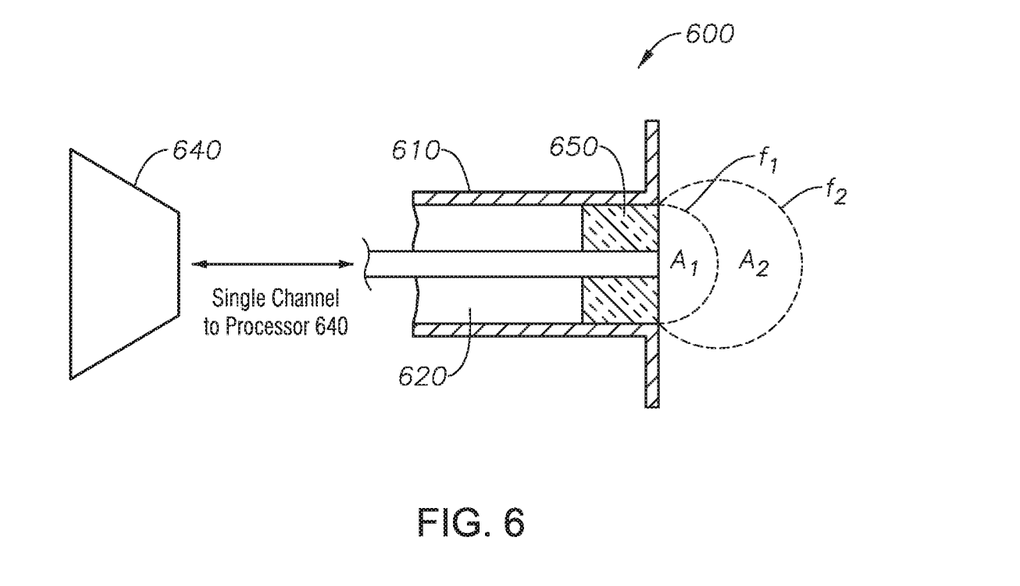
FIG. 6 is a schematic diagram of a single probe flow meter including a single coaxial probe operating at two frequencies for measuring an impedance characteristic of a multiphase mixture, in accordance with an embodiment of the invention.

FIG. 6 is a schematic diagram of a single probe flow meter including a single coaxial probe operating at two frequencies for measuring an impedance characteristic of a multiphase mixture, in accordance with an embodiment of the invention. In accordance with various embodiment, there is provided a single probe flow meter 600, which includes a conduit 610 to receive a mixture, and a single coaxial probe 620 operating at a dual frequency of excitation to minimize conductivity loss relative to capacitance. The single coaxial probe 620 measures an average complex permittivity of the mixture from a first area $A_1$ in front of the single coaxial probe 620 at a first frequency $f_1$ and an average complex permittivity of the mixture from a second area $A_2$ in front of the single coaxial probe 620 at a second frequency $f_2$. In accordance with certain embodiments of the invention, the first area $A_1$ is smaller than the second area $A_2$ and the first frequency $f_1$ is greater than the second frequency $f_2$, where the first and second frequencies range from 1 to 3 GHz. According to at least one embodiment, the respective sizes of the first area $A_1$ and the second area $A_2$ are based on, for example, the flow conditions of the multiphase mixture through the conduit 610. The single probe flow meter 600 further includes a single probe processor 640 that transmits an electromagnetic signal to the single coaxial probe 620 and receives a reflected electromagnetic signal from the single coaxial probe 620 using a single channel. The single probe processor 640 determines the presence of multiphase flow in the mixture based on the complex permittivity measured at the first and second frequencies $f_1$, $f_2$. In particular, the single probe processor 640 determines the presence of multiphase flow in the mixture by comparing the complex permittivity measured at the first and second frequencies $f_1$, $f_2$.

In accordance with certain embodiments of the invention, the single probe processor 640 normalizes the complex permittivity measured by the single coaxial probe 620 at the first and the second frequencies $f_1$, $f_2$ with respect to systematic variance as a function of frequency. For example, the single probe processor 640 normalizes the complex permittivity measured at the first and the second frequencies $f_1$, $f_2$ by separating the real and imaginary components of each complex permittivity and dividing one of the real and imaginary components by the other, resulting in a real ratio and an imaginary ratio, which can be monitored. Another example of how the single probe processor 640 normalizes the complex permittivity measured at the first and the second frequencies $f_1$, $f_2$ is by calculating the magnitude of the complex permittivity for each complex permittivity (i.e., taking the square root of the sum of the squares of the real and imaginary components), and dividing each calculated magnitude by its respective complex permittivity. One of ordinary skill in the art would have understood that other normalization methods could be used to normalize the complex permittivity measured by the single coaxial probe 620 at the first and the second frequencies $f_1$, $f_2$.

In accordance with an embodiment of the invention, the operation of the single coaxial probe 620 further includes at least one of an additional low frequency modulation on top, for example, 20 kilohertz (kHz), as a non-limiting example, and the use of frequency modulation techniques to measure different areas of the mixture in front of the coaxial probe 620.

Optionally, the single coaxial probe 620, according to an embodiment of the invention, measures the average complex permittivity of the mixture by performing one or more frequency sweeps of excitation of an area or areas of the mixture to measure dispersion of the mixture as a function of frequency. Assuming that the end of the coaxial probe operates similarly to a single slit in a diffraction experiment, the single coaxial probe 620 operates such that, as the wavelength of the excitation is increased, the area being measured by the single coaxial probe 620 scales with the wavelength (i.e., 1/f). Thus, frequency can be used to influence the area over the measurement so that the single coaxial probe 620 can measure a spatially averaged permittivity over a different area. Variations in the measured value can indicate a non-homogenous flow in the mixture (i.e., multiphase flow in the mixture).

Optionally, the conduit 610, as further shown in FIG. 6, includes a flow diffuser (not shown) contained therein for controlling the flow of the multiphase mixture through the conduit 610 and across the probe array 620 for sampling the multiphase mixture to determine, for example, the complex permittivity of the multiphase mixture across the entire cross-sectional area of the conduit 610. In accordance to some embodiments, the flow diffuser also homogenizes the multiphase mixture in the conduit 610.

Embodiments of the invention provide non-obvious advantages over conventional multiphase flow meters. For example, some embodiments of the invention are directed to a multiphase flow meter operating at a high measurement frequency to minimize a salinity loss signal relative to a water cut signal for measuring the water cut and salinity of a multiphase mixture having a high salinity concentration. Other embodiments of the invention utilize the relationship between measurement frequency and probe range capabilities to detect multiphase flows in a mixture. Certain embodiments incorporate frequency modulation techniques to maximize signal-to-noise ratio (SNR) and to probe differential permittivity in high salinity concentration, multiphase mixtures. Some embodiments provide a single coaxial probe to measure permittivity properties of a fluid mixture rather than individual fluid types separately. Accordingly, embodiments of the invention provide non-obvious advantages over conventional flow meters by providing a sensor device which is not sensitive to salinity changes in the multiphase mixture and which uses a single set of electronics to determine the presence of multiphase flow in a mixture and to optimize area coverage and dynamic range measurement of the water cut and salinity of the multiphase mixture having a high salinity concentration.

The present invention may suitably comprise, consist or consist essentially of the elements disclosed and may be practiced in the absence of an element not disclosed. For example, it can be recognized by those skilled in the art that certain steps can be combined into a single step.

Unless defined otherwise, all technical and scientific terms used have the same meaning as commonly understood by one of ordinary skill in the art to which this invention belongs.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur. As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that the mere use of the term "first" and "second" does not require that there be any "third" component, although that possibility is contemplated under the scope of the embodiments of the present invention.

Ranges may be expressed herein as from about one particular value, and/or to about another particular value. When such a range is expressed, it is to be understood that another embodiment is from the one particular value and/or to the other particular value, along with all combinations within said range.

All publications mentioned are incorporated by reference to disclose and describe the methods or materials, or both, in connection with which the publications are cited. The publications discussed are provided solely for their disclosure prior to the filing date of the present application. Nothing is to be construed as an admission that the invention is not entitled to antedate such publication by virtue of prior invention. Further, the dates of publication provided may be different from the actual publication dates, which may need to be independently confirmed.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

What is claimed is:

1. A flow meter for measuring water cut and salinity of a multiphase mixture, the flow meter comprising:
    a conduit configured to receive the multiphase mixture;
    a probe array configured to measure a cross-sectional area of the conduit, wherein the probe array comprises a plurality of coaxial probes connected in parallel; and
    a processor configured to
        ground all but one of the coaxial probes in the probe array,
        transmit a single signal to the probe array, and
        receive a single reflected signal from the probe array,
    wherein the processor is configured to transmit the single signal and receive the single reflected signal using a single channel between the probe array and the processor,
    wherein each of the plurality of coaxial probes is configured to receive the single transmitted signal,
    wherein each of the plurality of coaxial probes connected in parallel is configured to measure a single impedance characteristic of a same type across the cross-sectional area of the conduit based on the received single transmitted signal,
    wherein the single reflected signal received from the probe array comprises a single measured signal generated from combining each of the measured impedance characteristics from the plurality of coaxial probes connected in parallel,
    wherein the processor is configured to calculate the water cut and the salinity of the multiphase mixture based on a single complex permittivity of the multiphase mixture calculated from the received reflected signal of each non-grounded coaxial probe, and
    wherein the single complex permittivity is an average of the complex permittivity of the multiphase mixture measured by each non-grounded coaxial probe.

2. The flow meter of claim 1, wherein the processor is further configured to perform an interpolation between the complex permittivity of the multiphase mixture measured by each non-grounded coaxial probe to generate a single continuous function of complex permittivity throughout the cross-sectional area of the conduit.

3. The flow meter of claim 2, wherein the interpolation is a linear or bilinear interpolation.

4. The flow meter of claim 1, wherein the plurality of coaxial probes are arranged in a two-dimensional plane.

5. A method for measuring water cut and salinity of a multiphase mixture, the method comprising:
    receiving, using a conduit, the multiphase mixture;
    measuring, using a probe array, a cross-sectional area of the conduit, wherein the probe array comprises a plurality of coaxial probes connected in parallel;
    grounding all but one of the coaxial probes in the probe array;
    transmitting a single signal to the probe array; and
    receiving a single reflected signal from the probe array; and
    calculating, using a processor, the water cut and the salinity of the multiphase mixture based on a single complex permittivity of the multiphase mixture calculated from the received reflected signal of each non-grounded coaxial probe,
    wherein the single signal is transmitted and the single reflected signal is received using a single channel between the probe array and the processor,
    wherein each of the plurality of coaxial probes is configured to receive the single transmitted signal,
    wherein each of the plurality of coaxial probes connected in parallel is configured to measure a single impedance characteristic of a same type across the cross-sectional rea of the conduit based on the received single transmitted signal,
    wherein the single reflected signal received from the probe array comprises a single measured signal generated from combining each of the measured impedance characteristics from the plurality of coaxial probes connected in parallel, and wherein the single complex permittivity is an average of the complex permittivity of the multiphase mixture measured by each non-grounded coaxial probe.

6. The method of claim 5, further comprising:

performing an interpolation between the complex permittivity of the multiphase mixture measured by each non-grounded coaxial probe to generate a continuous function of complex permittivity throughout the cross-sectional area of the conduit.

* * * * *